US00PP25742P3

(12) United States Plant Patent
Turpin

(10) Patent No.: US PP25,742 P3
(45) Date of Patent: Jul. 28, 2015

(54) PEAR TREE NAMED 'ANP-0131'

(50) Latin Name: *Pyrus communis*
Varietal Denomination: ANP-0131

(71) Applicant: Susanna Turpin, Tatura (AU)

(72) Inventor: Susanna Turpin, Tatura (AU)

( * ) Notice: Subject to any disclaimer, the term of this patent is extended or adjusted under 35 U.S.C. 154(b) by 188 days.

(21) Appl. No.: 13/987,455

(22) Filed: Jul. 25, 2013

(65) Prior Publication Data

US 2015/0033422 P1 Jan. 29, 2015

(51) Int. Cl.
*A01H 5/08* (2006.01)

(52) U.S. Cl.
USPC ..... Plt./176

(58) Field of Classification Search
USPC ..... Plt./176
See application file for complete search history.

*Primary Examiner* — Susan McCormick Ewoldt
(74) *Attorney, Agent, or Firm* — Klarquist Sparkman, LLP

(57) ABSTRACT

A new pear variety distinguished by its medium to large sized fruit and long storage potential. Fruit are bicoloured with a strong red blush over a green colored skin. They ripen to a fine texture with no grit and excellent aromatics.

6 Drawing Sheets

Latin name of the genus and species of the plant claimed: *Pyrus communis.*

Variety denomination: 'ANP-0131'.

CROSS REFERENCE TO RELATED APPLICATIONS

None

STATEMENT REGARDING FEDERALLY SPONSORED RESEARCH OR DEVELOPMENT

None

BACKGROUND OF THE INVENTION

The present invention relates to a new and distinct variety of pear tree named 'ANP-0131'. My new tree resulted from a planned hybridization program and is a selection from crossing 'Corella' (Unpatented) as the seed parent with 'Doyenne du Comice' (Unpatented) as the pollen parent.

The cross was made in 1995 at Stoneville, Western Australia and the population of 182 seedlings established at Tatura, Victoria, Australia. The seedling tree of the 'ANP-0131' variety was selected in 2001 and planted into a replicated trial on 'D6' (unpatented) rootstock and 'Quince A' (unpatented) rootstock with 'Beurre Hardy' (unpatented) pear as an interstock in 2003 . Additional trees of the seedling selection were planted at Australian Pome Fruit Improvement Program (APFIP) sites in Western Australia, South Australia and Victoria in the same year for regional evaluation. Further asexual propagation by budding and grafting of trial trees in 2009 and 2012 for large scale evaluation trials at Tatura on 'BP1' rootstock (U.S. Plant Pat. No. 10,231) showed that the foregoing characteristics come true to form, are firmly fixed, and are established and transmitted through succeeding propagations.

BRIEF SUMMARY OF THE INVENTION

The 'ANP-0131' variety is distinguished from other pear varieties due to the following unique combination of characteristics: bicoloured fruit with a strong dark red overcolour and green colored skin that does not change color upon softening. Fruit can be stored long term similar to the green coloured pear variety 'Packhams' Triumph' (not patented) without loss in eating quality and ripen to a soft, fine texture low in grit.

The new variety was determined to be distinct from the parent varieties 'Corella' and 'Doyenne du Comice' by the following characteristics: The time of full bloom for ANP-0131 is between that of its parents with 'Corella' being early and 'Doyenne du Comice' later flowering. Maturity for consumption of 'ANP-0131' is medium whilst 'Corella' and 'Doyenne du Comice' are both late. Whilst all have fine melting texture, 'ANP-0131' requires less time in storage than 'Corella' to initiate softening and has lower grit under the skin and around the core than 'Doyenne du Comice'. The expression of flavor is greater than that of Corella but less than the strong flavor and aromatics of 'Doyenne du Comice'. The skin overcolor has a uniform coverage and a darker red color compared to Corella that has a bright red overcolor concentrated around lenticels. Under environmental conditions at Tatura 'Doyenne du Comice' does not usually develop a red overcolor. The following detailed description concerns the original tree, selected on January 2001, and progeny first asexually propagated in 2003. The original tree and progeny have been observed growing in a cultivated area in Goulburn Valley, Australia.

Certain characteristics of this variety may change with changing environmental conditions (such as photoperiod, temperature, moisture, soil conditions, nutrient availability, or other factors). For example, leaf colors may be brighter green if the trees are grown in soil with greater nitrogen concentrations, and may be more yellow when grown in soil containing lesser amounts of nitrogen. Color descriptions and other terminology are used in accordance with their ordinary dictionary descriptions, unless the context clearly indicates otherwise. Color designations (hue/value/chroma) are made with reference to The Royal Horticultural Society Colour Chart (R.H.S.) version 2 published in 1966.

Figure 1:
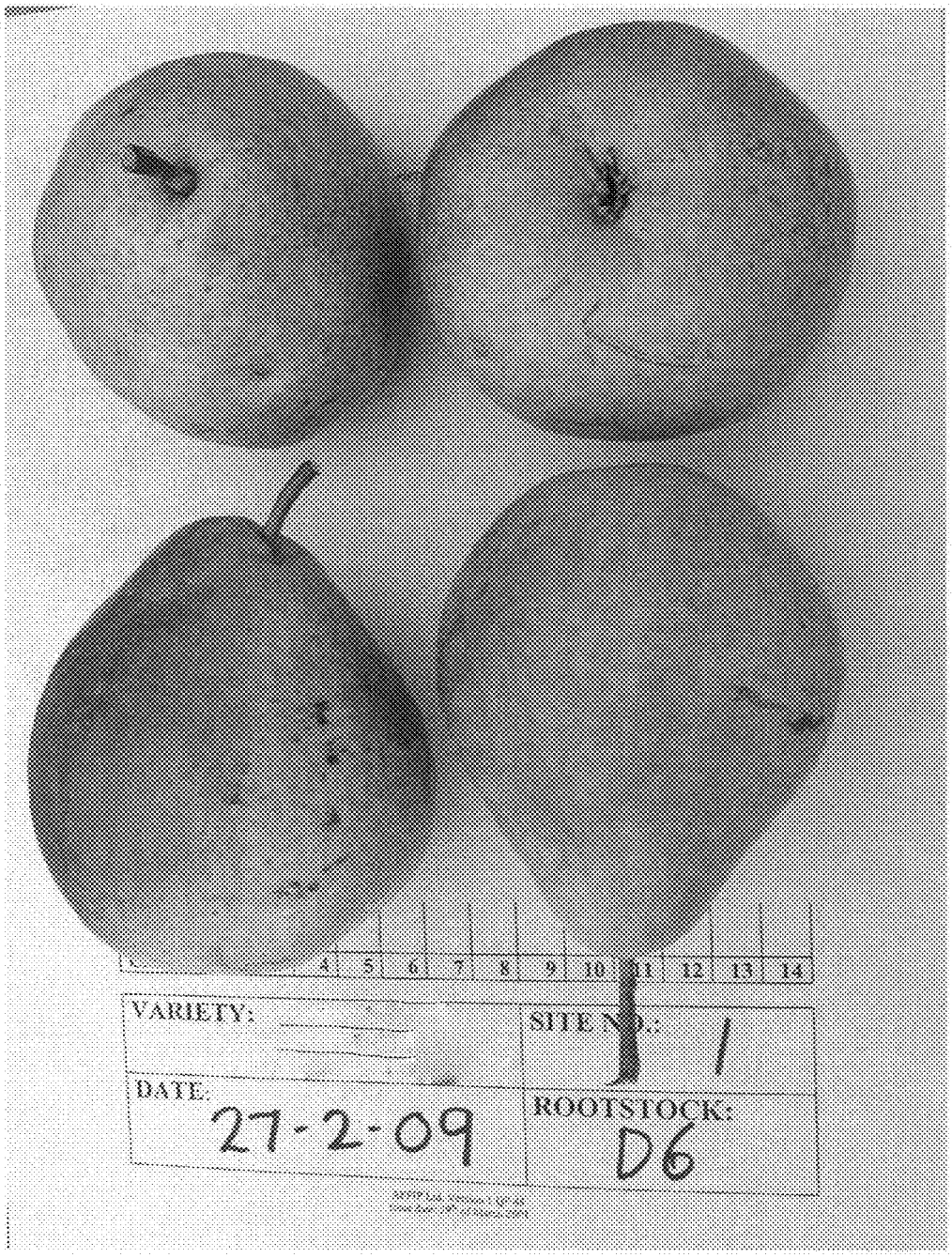
FIG. 1 is a photograph showing the stem end, calyx end and side view of typical fruit of 'ANP-0131'.
Figure 2:
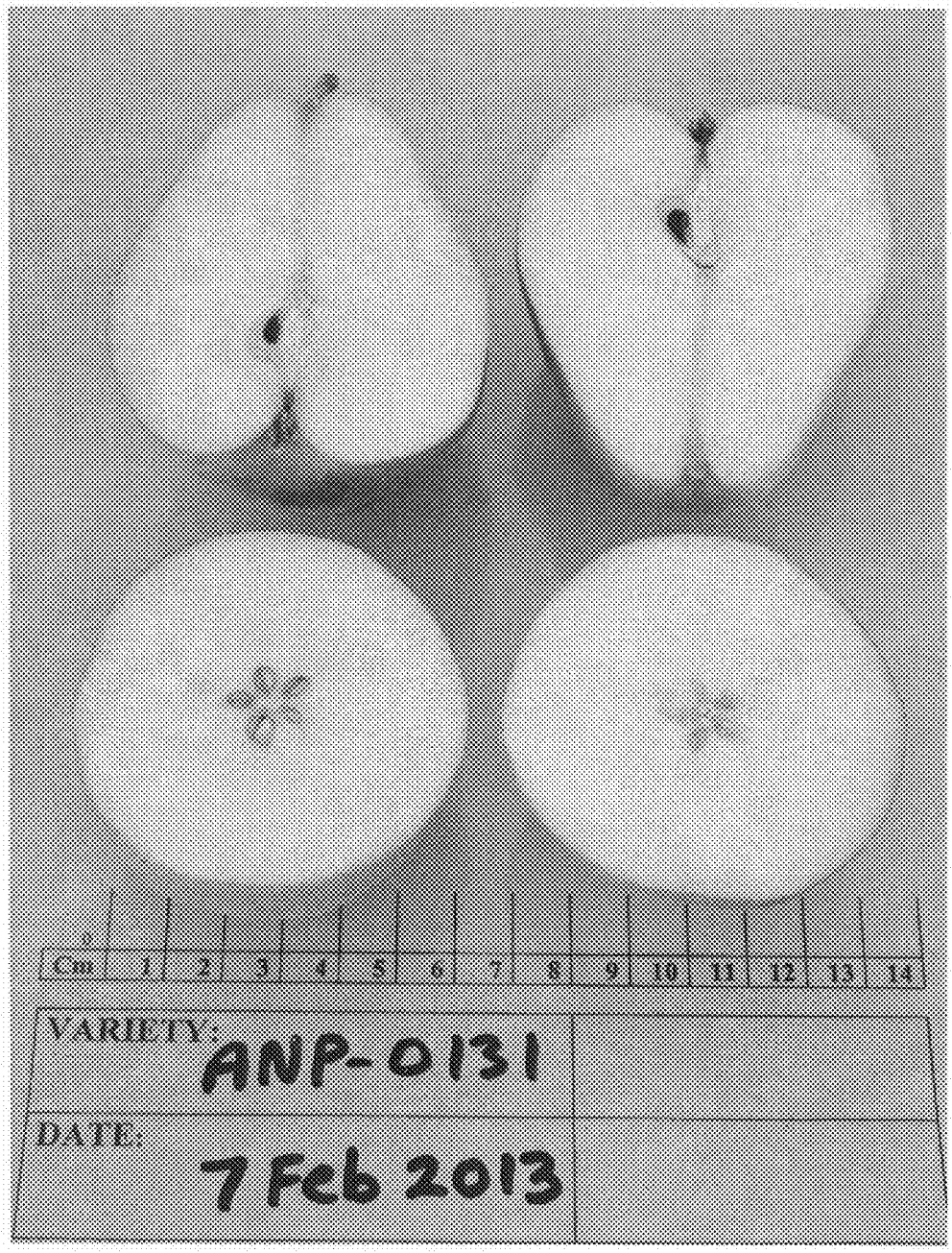
FIG. 2 is a photograph showing the horizontal and vertical cross sectional view of typical fruit of 'ANP-0131'.
Figure 3:
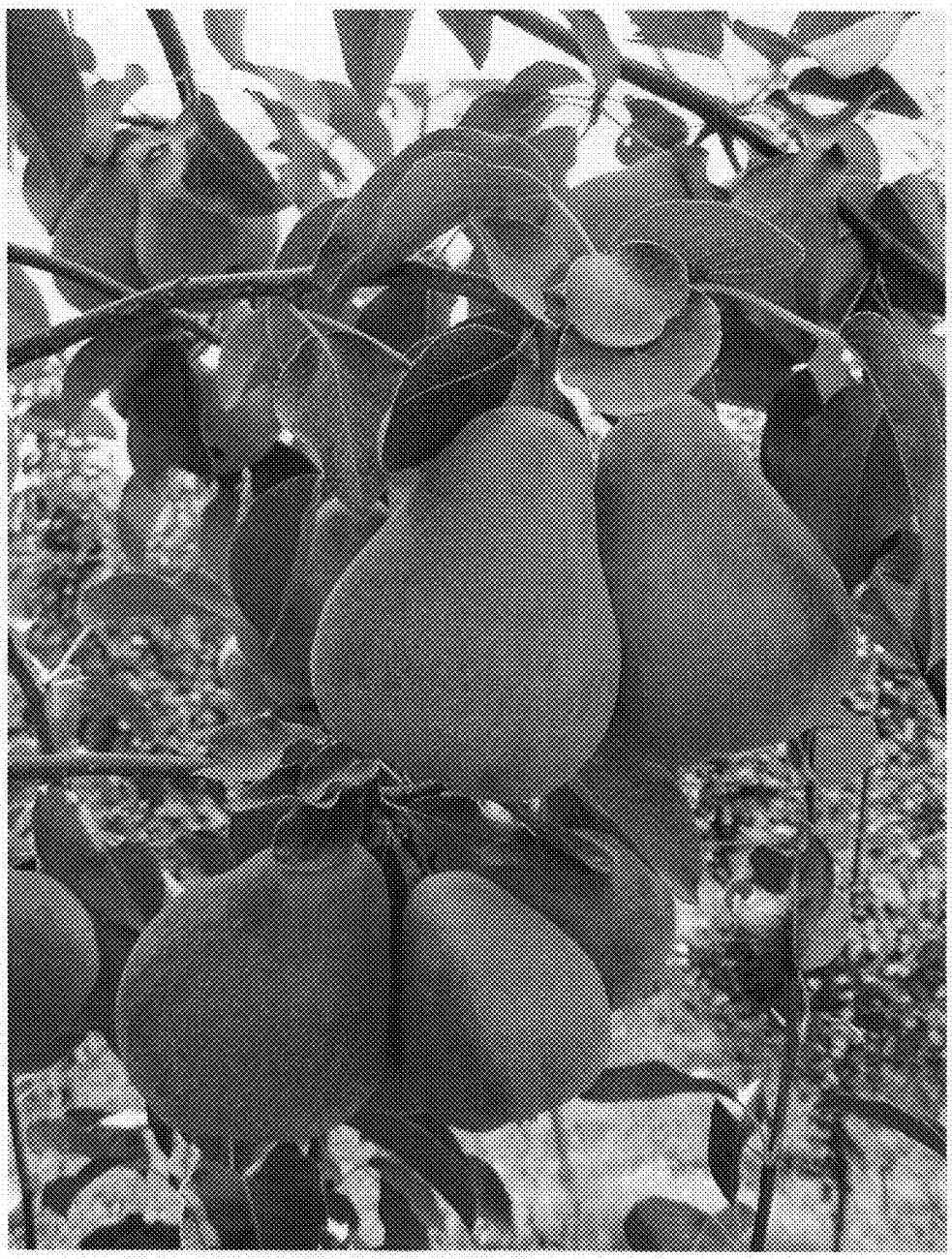
FIG. 3 is a photograph showing typical fruit on a tree of 'ANP-0131'.
Figure 4:
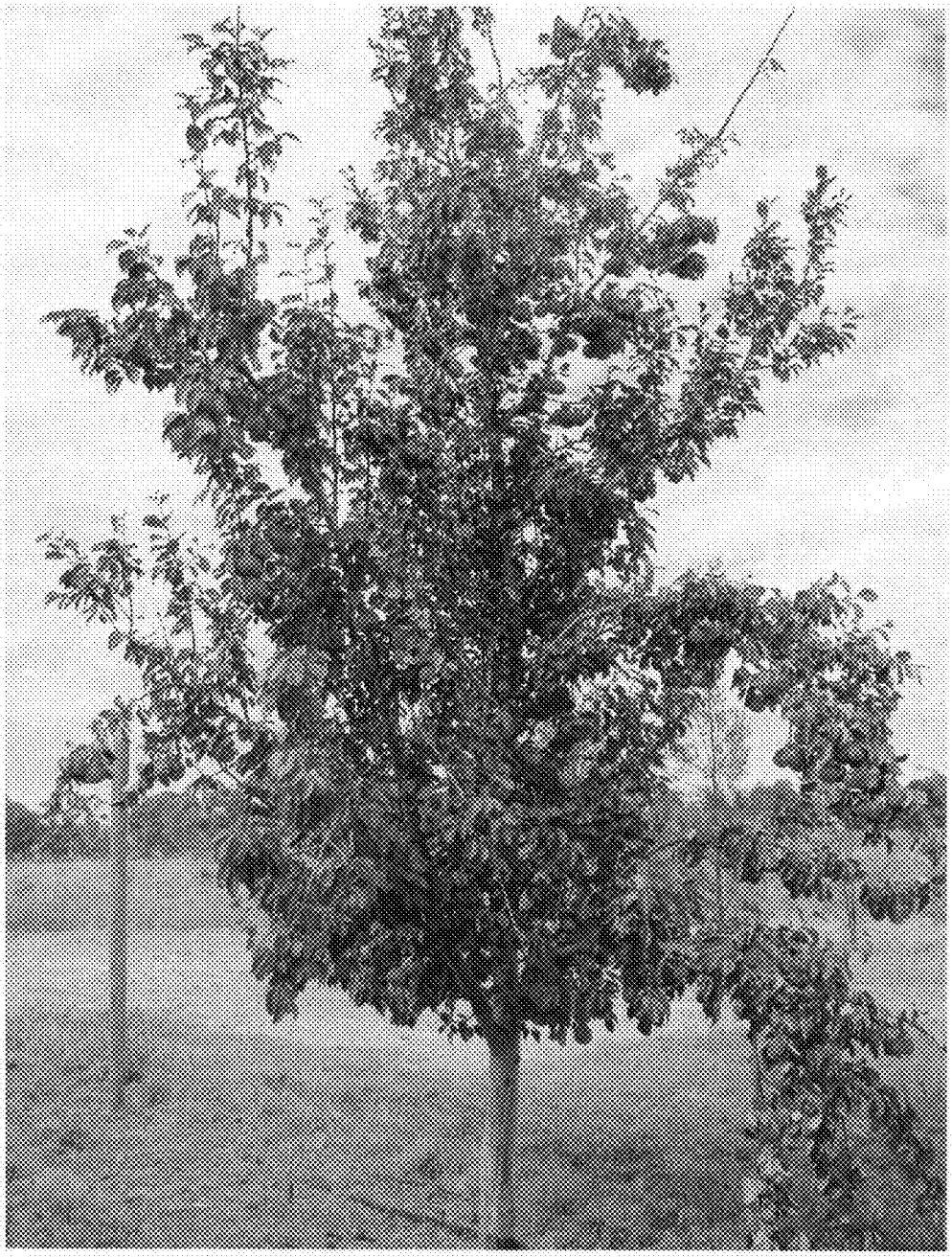
FIG. 4 is a photograph showing a 10 year old tree of 'ANP-0131' on D6 rootstock.
Figure 5:
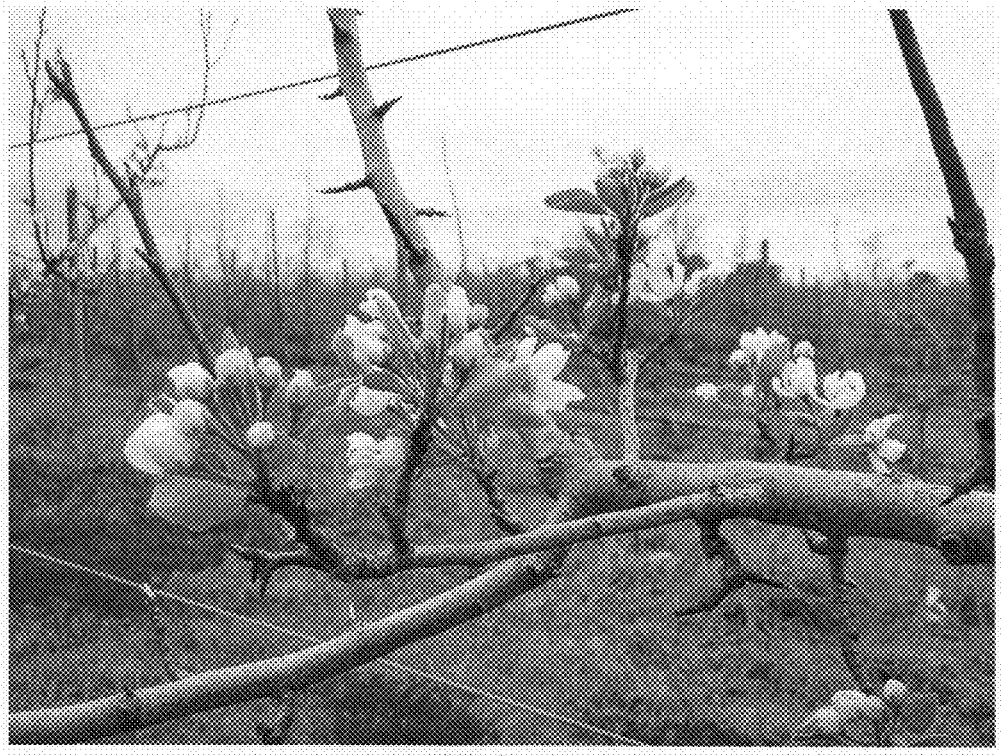
FIG. 5 is a photograph showing a flowering branch of 'ANP-0131'.
Figure 6:
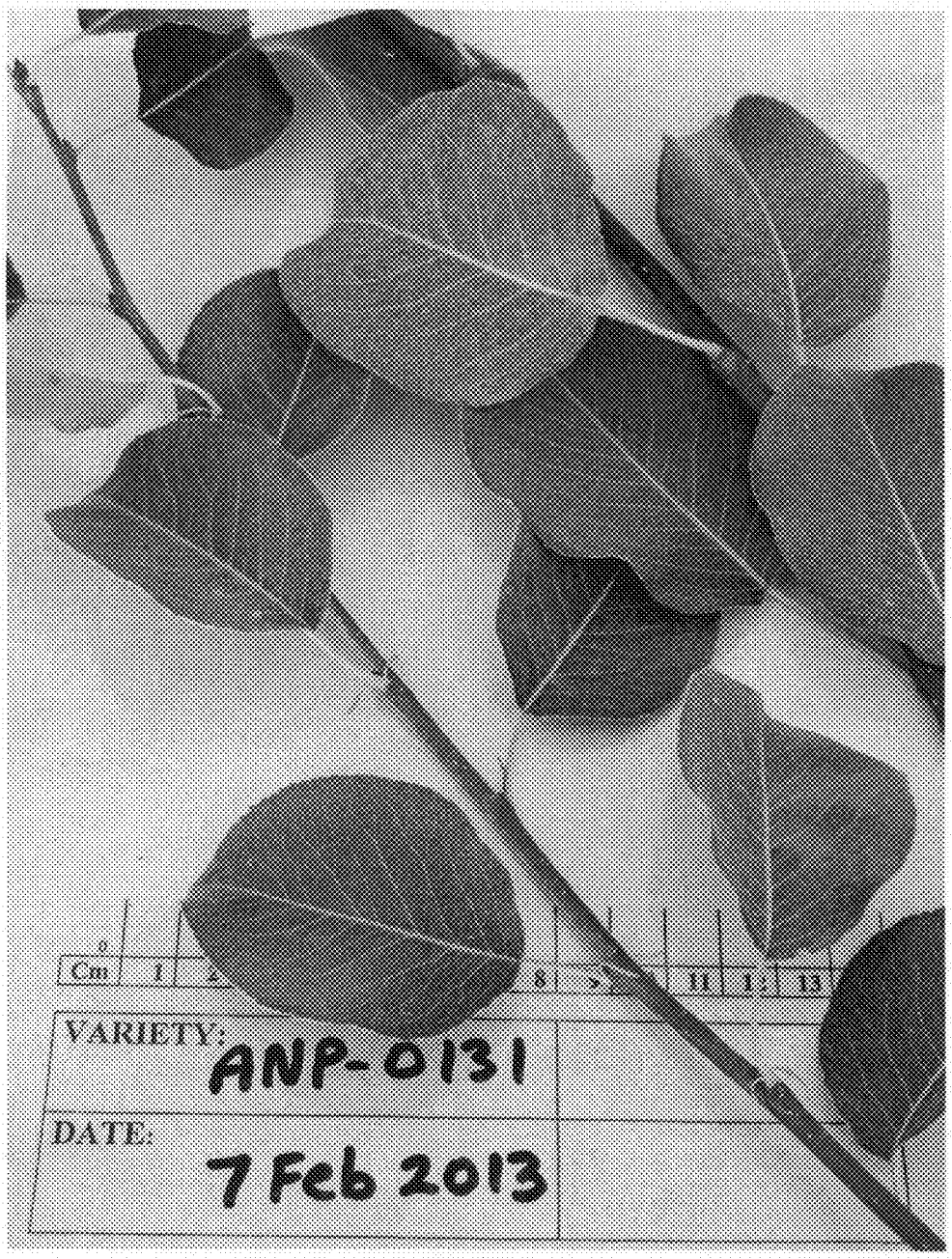
FIG. 6 is a photograph showing the typical mature leaves of 'ANP-0131'.

The color photographs show typical specimens of the leaves and fruit of this new pear tree variety at 10 years old and depict the color as nearly true as is reasonably possible to make the same in a color illustration of this character. It should be noted that colors may vary, for example due to lighting conditions at the time the photograph is taken. Therefore, color characteristics of this new variety should be determined with reference to the observations described herein, rather than from the photographs alone.

DETAILED DESCRIPTION

Botanical

The following detailed description of the 'ANP-0131' variety is based on observations of asexually reproduced progeny. The observed progeny are trees which were 10 years of age and growing on D6 (*Pyrus calleryana*) variety rootstock in Goulburn Valley, Australia.

Scientific name: *Pyrus communis* 'ANP-0131'.

Parentage:

- *Seed parent*.—'Corella', a seedling selection of unknown parentage developed by German settlers in the Barossa Valley in South Australia in the late 19th century.
- *Pollen parent*.—'Doyenne du Comice', which was a seedling from fruit garden of Comice Horticole, Angers, Department of Maine-et-Loire, France, 1849.

Tree:

- *Vigor*.—Vigorous.
- *Overall shape*.—Tree habit semi-upright.
- *Height*.—Between 3 to 5 m.
- *Width*.—Overall spread between 1.5 to 2.5 m.
- *Caliper*.—24.1 cm at 20 cm above the graft union.
- *Trunk bark texture*.—Smooth with few cracks.
- *Trunk bark color*.—Medium grey (RHS 201C).
- *Patches or other markings*.—Lenticels greyed-orange in colour (RHS 177A).
- *Primary branches*.—Semi-upright. Angle of emergence from trunk: About 45 degrees.
- *Branch color*.—One year old wood greyed-brown (RHS 199A). Two year old wood greyed-brown (RHS 199B).
- *Branch pubescence*.—None.
- *Branch lenticels*.—High density, approximately 18.8 per cm2 (s.d. 3.9), round shape, typically 0.6 to 1.2 mm in diameter; color greyed-brown (RHS 199D).
- *Internodes*.—Average length 2.7 cm (s.d. 0.8) on one year old wood. Average length 2.5 cm (s.d 0.5) on two year old wood.
- *Bearing*.—Annual.
- *Hardiness*.—Average in area tested.
- *Disease resistance*.—No specific testing for relative plant disease resistance has been undertaken. Under observation in 2012 in Goulburn Valley, Australia slight resistance to field infection of pear scab was observed in the leaves and fruit.
- *Pollination*.—Cross compatible with 'Hosui' (not patented), 'Corella' and ANP-0118 (Serial No.20150033423), but incompatible with 'Packhams' Triumph'.

Leaves:

- *Texture*.—Smooth upper and lower surfaces.
- *Sheen*.—Glossy.
- *Length*.—About 49 mm to about 71 mm. Averaging 60 mm (s.d. 5).
- *Width*.—About 34 mm to about 56 mm. Averaging 44.6 mm (s.d. 6.6).
- *Thickness*.—About 0.18 mm to about 0.26 mm. Averaging 0.22 mm (s.d. 0.02).
- *Petiole*.—About 24.7 mm (s.d. 4.1) long and about 1.1 mm (s.d. 0.2) in diameter; Yellow-green (RHS 154C) in color.
- *Margin*.—Serrate.
- *Tip shape*.—Cuspidate.
- *Stipules*.—Commonly 2 per leaf bud.
- *Leaf color*.—Upper leaf surface: Yellow-green (RHS 146A). Lower leaf surface: Yellow-green (RHS 147B). Vein: Yellow-green (RHS 154D) pinnate with net-like minor veins.
- *Pubescence*.—Upper and lower leaf surfaces weak to absent. The length, width, thickness and other measurements were obtained from observations of 20 typical leaves in Goulburn Valley on 15 Jan. 2013.

Flowers:

- *Size*.—Medium, approximately 30.4 mm in diameter.
- *Shape*.—Ovoid to round.
- *Color*.—Unopened bud: white in color (RHS 155D). Opened flower: white in color (RHS 155D).
- *Petals*.—5 petals per flower; each petal is obovate in shape; about 12.0 mm long and 7.6 mm wide. White in color (RHS 155D).
- *Stamen*.—18 to 20 per flower; each stamen is 5.4 to 7.7 mm long and white in color (RHS 155D). Arranged in a single row.
- *Anthers*.—Red purple (RHS 59B) in color.
- *Pistil*.—Stigma is about 0.1 mm long; rounded at top in shape; 5 styles, and light yellow green (RHS 145B) in color.
- *Sepals*.—About 4.9 mm long and 2.3 mm wide mm wide (at base); Acuminate in shape; yellow green (RHS 144B) in color.
- *Pollen*.—Yellow (RHS 15A) in color.
- *Fragrance*.—Faint.
- *Bloom season*.—14-23 September in Goulburn Valley, Australia; average full bloom date from 2009 to 2012 was 23 September for ANP0131; 29 September for Packham's Triumph.

Fruit: (Observations from 20 fruit in the 165 to 175 g weight range harvested in Goulburn Valley, Australia).

- *Size*.—Medium to large; About 68 mm long and 66 mm wide to 89 mm long and 70 mm wide.
- *Form*.—Obovate pyriform to turbinate; symmetric, 1.19 length to diameter ratio.
- *Cavity*.—None; sepals closed.
- *Basin (blossom end)*.—About 3.8 mm deep and about 18 mm wide.

*Stem*.—About 21 mm long and 2.6 mm in diameter; yellow-green (RHS 150B) in color; greyed-orange (RHS 163A) overcolour.

*Locules*.—Small; 5 locules; open.

*Skin*.—Thin with matt finish; no tendency to become waxy in storage.

*Color*.—General color effect: sun blush; typically 20 to 40% skin coverage and up to 70% skin coverage dependent upon sun exposure. Lenticels not conspicuous; small and round; yellow-green in color (RHS 144A). Ground color: Yellow-green (RHS 144B). Overcolor: Greyed-purple to Greyed-red (RHS 183A to 178A dependent upon intensity of blush). Russetting: Absent.

*Fruit properties during harvest period in Goulburn Valley, Australia*.—Acid content: about 155 g/100 ml malic acid. Firmness: 5 to 6.5 kg for green fruit and softens about 0.4 kg after 7 weeks in storage at 0° C. Soluble solids: about 13 to 16° brix at harvest, average 15.7° brix (s.d. 0.7) after 7 weeks in storage at 0° C. in 2013. Starch index: on a scale of 1 (100% starch) to 6 (no starch) average 2.3 for green fruit. Flavor: balanced acid/sugar ratio, medium sweetness. Juiciness: medium. Flesh color: white (RHS 155A). Flesh texture: fine; no grit cells. Aroma: Slight.

*Core*.—Basal bundle area shape about 21.3 cm (s.d. 2.1) long and 19.1 cm (s.d. 1.5) wide; calyx tube semi-closed; core line definition medium.

*Seed*.—Up to 10 seed per fruit, average 2.9 seed (s.d. 1.7) in 2013 and 1 to 2 seed per locule; tear drop shape; about 9.2 mm (s.d. 0.5) long and 5.5 mm (s.d. 0.4) wide; yellow-orange color at harvest (RHS 20C).

*Fruit production*.—Harvest period mid February in Goulburn Valley, Australia. First harvest date 11 February and last harvest date 1 March dependent upon seasonal conditions. Production per hectare not determined. Trees produce consistent medium crop loads similar to 'Corella'.

*Storage*.—Fruit remains fresh at room temperature for at least 7 days and can be stored for up to 10 months under controlled atmosphere.

*Usage*.—Fresh market.

I claim:

1. A new and distinct variety of pear tree, substantially as herein shown and described.

* * * * *